United States Patent [19]

Menson et al.

[11] 4,233,403
[45] Nov. 11, 1980

[54] AMYLASE ASSAY

[75] Inventors: Robert C. Menson, Newport Beach, Calif.; Venkatachalam Narayanswamy; Richard C. Burns, both of Wilmington, Del.

[73] Assignee: E. I. Du Pont de Nemours and Company, Wilmington, Del.

[21] Appl. No.: 881,669

[22] Filed: Feb. 27, 1978

Related U.S. Application Data

[63] Continuation-in-part of Ser. No. 704,976, Jul. 13, 1976, abandoned.

[51] Int. Cl.³ .............................................. C12Q 1/40
[52] U.S. Cl. ...................................... 435/22; 435/810
[58] Field of Search ................ 195/103.5 R, 103.5 S, 195/99, 63; 23/230 R; 435/22, 810

[56] References Cited

U.S. PATENT DOCUMENTS

| | | | |
|---|---|---|---|
| 3,476,515 | 11/1969 | Johnson et al. | 23/230 R |
| 3,879,263 | 4/1975 | Adams | 195/103.5 S |
| 4,000,042 | 12/1976 | Adams | 195/103.5 S |
| 4,009,079 | 2/1977 | Tsujino et al. | 435/22 X |
| 4,102,749 | 7/1978 | Driscoll et al. | 435/22 |

FOREIGN PATENT DOCUMENTS 2602542 7/1976 Fed. Rep. of Germany .

OTHER PUBLICATIONS

Hamley G. G. The Condensed Chemical Dictionary, 8th ed. Van Nostrand Reinhold Co. N. Y., 1971 (pp. 346, 419 and 539).
Jansen et al. α-(p-Nitrophenyl) Maltocide as a Substrate for the Assay of Amylase. Nature, vol. 182, 1958 (pp. 525-526).
Driscoll, et al., A New Method for the Determination of Amylase 173rd ACS Meeting, New Orleans, Louisiana 3/1977, Abstract No. 117.

*Primary Examiner*—David M. Naff

[57] ABSTRACT

Disclosed herein are a method and a reagent test kit, both using an improved substrate to measure the amylase content of a sample. The substrate used is a glycoside consisting of a defined polysaccharide glycosyl residue and a substituted aromatic radical attached to the terminal unit of the glycoside. When detached from the polysaccharide, the aglycone exhibits a different spectral absorbance than the substrate.

15 Claims, 2 Drawing Figures

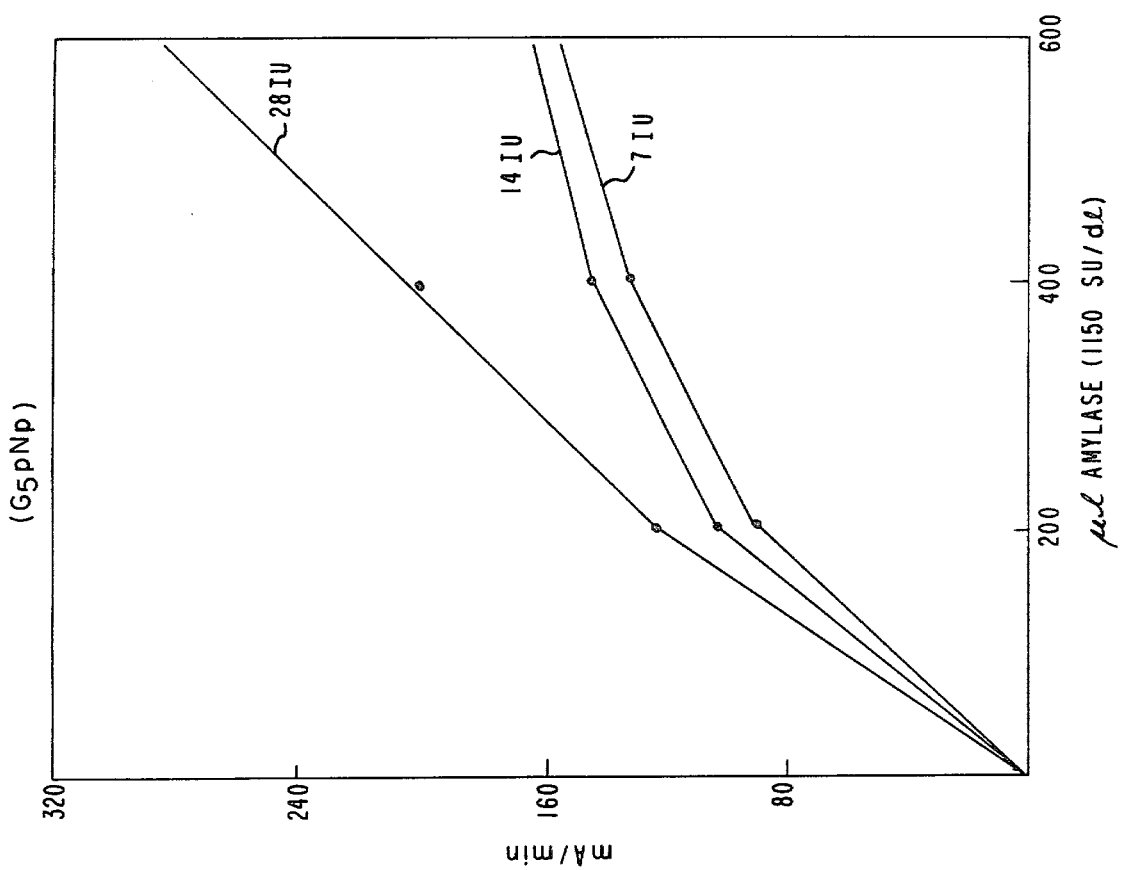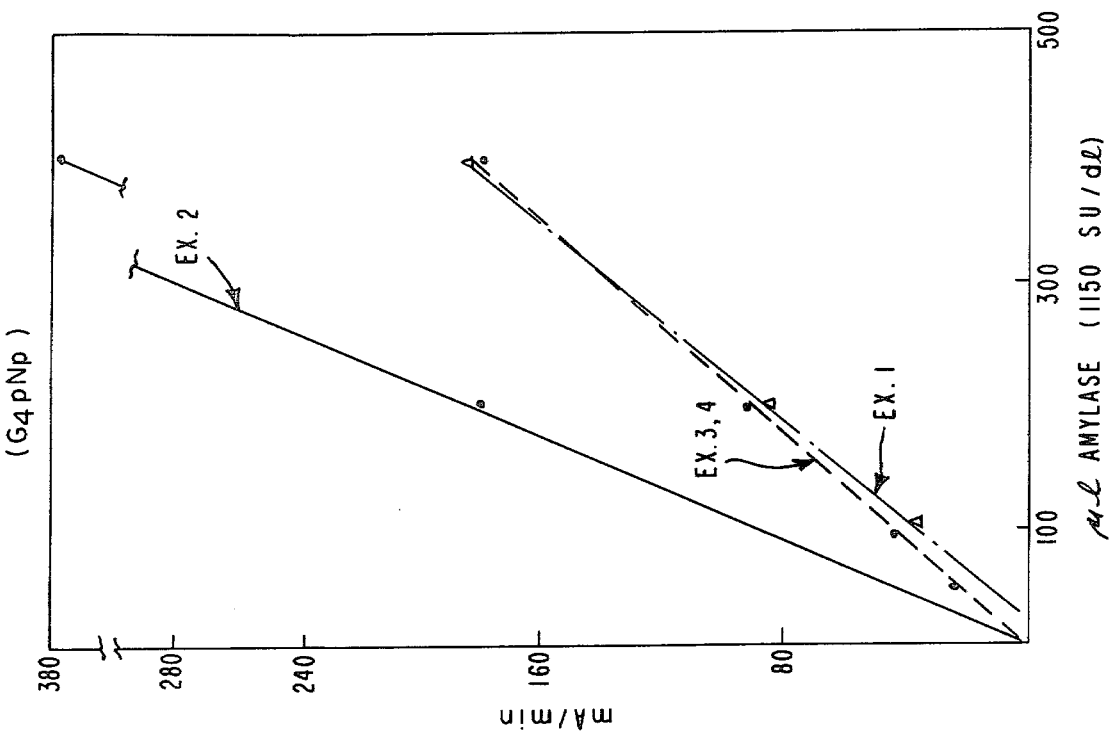

AMYLASE ASSAY

CROSS REFERENCE TO RELATED APPLICATION

This application is a continuation-in-part of copending application U.S. Ser. No. 704,976, filed July 13, 1976, now abandoned.

BACKGROUND OF THE INVENTION

1. Field of the Invention:

This invention relates to amylase assays and to a reagent test kit for use in such assays. More particularly, it relates to amylase assays in which a polysaccharide is used as the amylase substrate.

2. Discussion of the Prior Art:

α-Amylase is an enzyme which hydrolyzes the α[1→4] linkages between the glucose units in starch and the lower polymers and oligomers of glucose. This enzyme is produced in the human body, primarily in the pancreas and in the salivary glands, and its concentration in various body fluids is a useful diagnostic tool for physicians. For example, in healthy individuals, serum α-amylase levels are relatively constant, but they rise in response to pathological conditions, such as acute pancreatitis.

U.S. Pat. No. 3,879,263, issued Apr. 22, 1975, and U.S. Pat. No. 4,000,042, issued Dec. 28, 1976, disclose a process and reagent test kit for use in determining the α-amylase content of a sample using the defined oligosaccharides maltotetraose, maltopentaose or maltohexaose as the amylase substrate. The reaction between α-amylase and these substrates, preferably in the presence of a maltase, produces a specific amount of glucose which can be measured by any conventional glucose detection system. The additional glucose detection step is an inconvenience. Furthermore, if glucose is present in the sample, it must either be removed or compensated for. Although this can be done by conventional techniques, it is an extra step in the process which is a disadvantage.

A. P. Jansen and P. G. A. B. Wydeveld, Nature, 182, 525 (1958) postulate that α-(p-nitrophenyl)maltoside could be a substrate for an amylase assay. However, this paper shows that the authors never identified the active agent responsible for their observations. They reported: (1) Incubation of samples of human urine, saliva, duodenal contents and only incidentally serum with α-(p-nitrophenyl)maltoside at 37° for 16 hours produces 4-nitrophenol, identified spectrophotometrically by mixing the hydrolyzate with 0.02 N sodium hydroxide. (2) The hydrolysis was inhibited by protein precipitants such as 10% trichloroacetic acid and 0.5 N silver nitrate. (3) The hydrolysis was pH-dependent, being most effective at pH 5.9–7.0. They state that this experiment could not include "the possible existence of an unidentified carbohydrase" causing the observed activity. α-(4-Nitrophenyl)maltoside is not believed to be useful for human amylase assay because the cleavage of this compound by α-amylase is extremely slow. In contrast to the teaching of Jansen et al., the method of this invention produces amylase analyses in one hour or less.

SUMMARY OF THE INVENTION

According to the present invention, there is provided a rapid method for determining the amylase content of a sample comprising the steps of:

(a) adding to a solution containing a measured amount of the sample a defined polysaccharide substrate having the following formula:

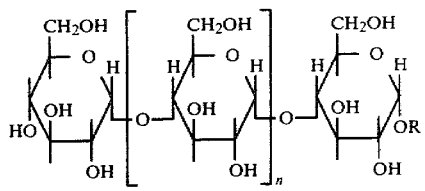

where n is 2, 3 or 4, and R is a substituted aromatic radical which, as a detached aglycone exhibits a different spectral absorbance than the substrate; and (b) monitoring the spectral absorbance of the solution. The measurement of the spectral absorbance can be made within one hour or less after the reaction between the sample and the substrate is initiated.

In the preferred embodiment, R is a substituted aromatic radical selected from the group consisting of

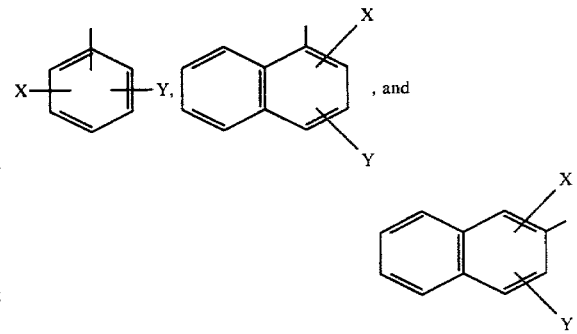

in which X and Y are individually selected from the group consisting of H, $NO_2$, halogens, alkyls of from 1 to 4 carbon atoms, $OR'$ or $CO_2R'$ where $R'$ is an alkyl group of from 1 to 6 carbon atoms, and at least one of X and Y is $NO_2$.

In the most preferred embodiment, the terminal glycoside unit is an α-(4-nitrophenyl) glycoside, and a maltase is also added to the solution.

A reagent test kit is also provided. This test kit contains one of the substrates listed above and a maltase.

DETAILED DESCRIPTION OF THE INVENTION

The following disclosure, and the invention it describes, is restricted to polymers and oligomers of glucose which are α[1→4] linked and which have a substituted aromatic radical attached to the terminal (reducing) glucose unit. Such compounds are represented by the general formula

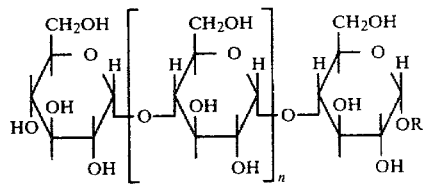

where n is an integer, R is the substituted aromatic radical, and the remaining portion of the compound is the glycosyl residue. When detached from the glycosyl residue by hydrolysis, the radical R becomes a phenol, ROH, or an anion of that phenol, RO⁻, (depending upon the condition of the solution) both of which are normally referred to as an aglycone.

This compound, which functions as a substrate for amylase, is a defined oligosaccharide. The term "defined" as applied to polysaccharides has, in the past, been used in a loose sense, often referring to any mixture of polysaccharides in which the relative percentages of the various polymers and oligomers are known. As used herein, however, the term "defined oligosaccharide" shall mean a substance containing at least 90% of an oligosaccharide with a given chain length, i.e., where n is a given integer.

α-Amylase acts as a catalyst in the hydrolysis of polysaccharides into small chain polysaccharides and eventually into maltose. It has been found and reported in the patents listed above that from among all polysaccharides, maltotetraose ($G_4$), maltopentaose ($G_5$) and maltohexaose ($G_6$) are preferred for use as a substrate in an amylase assay. The $G_m$ nomenclature is a convenient shorthand for m $\alpha[1\rightarrow4]$ linked glucose units where m is equal to n+2.

These three substrates are preferred for kinetic and stoichiometric reasons. The binding constant of α-amylase to polysaccharides increases as the number of $\alpha[1\rightarrow4]$ bonds increases, up to about $G_6$ where it levels off. For homologs lower than $G_4$, the binding constant is too small to give reasonable reaction rates. For homologs higher than $G_6$, even though the reaction proceeds rapidly, the results are not stoichiometric. Unproductive reactions occur so that m glucose units are not formed when α-amylase reacts with $G_m$. Furthermore, the maximum velocity of substrate release from α-amylase decreases with decreasing m. Where the detection system involves glucose and $G_m$ is used as the substrate, then, within a reasonable time, m glucose units should be produced for every α-amylase interaction with $G_m$. Otherwise, the percentage of the total glucose units released compared to those available must be estimated and this leads to error. These factors make $G_4$, $G_5$, and $G_6$ the preferred substrates.

As explained in U.S. Pat. No. 3,879,263, the use of a maltase such as α-glucosidase is not necessary in the measurement of either pancreatic or total α-amylase. Furthermore, since the present invention is not dependent upon glucose detection, maltase does not appear to even be necessary in assays for salivary α-amylase using the substrates of the present invention. However, the use of a maltase does increase the reaction rate in all circumstances. It is particularly useful to achieve a truly stoichiometric reaction, because the reaction rate of the maltase with the lower oligosaccharides is greater than the reaction rate of α-amylase with those substrates. α-Amylase acts to hydrolyze the substrate into smaller fractions, and the maltase acts to complete the hydrolysis to glucose units, so that the release of the substituted phenol occurs stoichiometrically. For this reason, oligosaccharides of the formula given above, with n=2, 3 or 4 are the most preferred substrates for the present invention. The discussion which follows, therefore, will be limited to those substrates, particularly those where n is 2 or 3. This limitation, however, is for convenience and is not intended to limit the disclosure.

When a maltase, such as α-glucosidase is used, a side reaction which gives rise to a blank rate occurs because of the reactivity of the maltase with the substrate. This means that even in the absence of α-amylase, there will be release of the phenol. Since the maximum velocity of product release from maltase decreases with increasing n, the growth of a blank rate is slower as n increases. One would expect, then, that the blank rate for $G_5$ would be less than that for $G_4$. This is verified by experimentation. However, an additional factor is involved in the choice between higher and lower oligosaccharides (i.e., $G_4$ or $G_5$) as the substrate. In all reactions of the substrate with amylase and reactions of maltase with the substrate, the rate increases, as a function of substrate concentration, to an optimum, at which point it levels off. The substrate concentration at which optimization occurs appears to increase with increasing n so that more of the substrate (and the maltase) must be used to optimize (linearize) the standard curve. For expensive chemicals, this is an important consideration.

The substrates of the present invention are the defined polysaccharides covered by the formula given above in which n is 2, 3 or 4 and R is a substituted aromatic radical which, when detached from the polysaccharide in the form of a phenol or a phenolate anion, exhibits a different spectral absorbance than the substrate. There are a large number of such radicals. Chief among them, however, are those radicals selected from the group consisting of

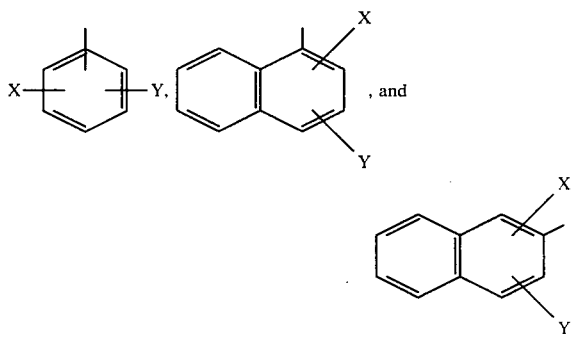

in which X and Y are individually selected from the group consisting of H, $NO_2$, halogens, alkyls of from 1 to 4 carbon atoms, OR' or $CO_2R'$; where R' is an alkyl of from 1 to 6 carbon atoms, and at least one of X and Y is $NO_2$. The anions of the phenols formed when these radicals are separated from the glycosyl residue have a maximum absorbance $\lambda_{max}$ of between about 290 and about 600 nm.

The details of the procedures for preparing these preferred compounds is set forth in U.S. Patent Applications Ser. No. 704,975 and Ser. No. 704,974, filed on the same day as this application.

The nitroaromatic glycosides useful in this invention are prepared by:

(a) contacting an acetylated glycoside of the formula

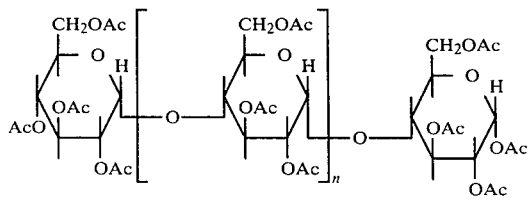

wherein Ac is an acetyl group, and n is an integer defined above, with a phenol selected from the group consisting of

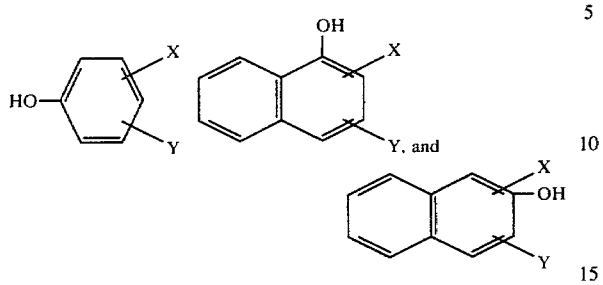

wherein X and Y are individually H, NO₂, halogen, alkyl of 1 to 4 carbon atoms, OR' or CO₂R' where R' is an alkyl group of 1 to 6 carbon atoms, with the proviso that only one of X and Y is NO₂, in the presence of a catalyst at a temperature in the range of about 80°–120° C.;

(b) nitrating the product of (a) by contacting said product with
  (i) nitric acid contained in a mixture of acetic acid and sulfuric acid, or
  (ii) a nitronium compound selected from nitronium, tetrafluoroborate, nitronium hexafluorophosphate and nitronium, trifluoromethanesulfonate contained in dichloromethane, chloroform or 1,2-dichloroethane; and (c) deacetylating the product of (b) by contacting said product with
  (i) a catalytic amount of an alkali metal lower alkoxide contained in the corresponding alcohol, or
  (ii) a solution of anhydrous ammonia or HCl in methanol.

Among the preferred embodiments, two compounds are particularly preferred; those in which n is 2 or 3 and R is 4-nitrophenyl. These compounds, α-(4-nitrophenyl) maltotetraoside (G₄pNp) and α-(4-nitrophenyl) maltopentaoside (G₅pNp), are used to determine the amylase content of a sample, such as blood serum or urine, according to the following reaction scheme

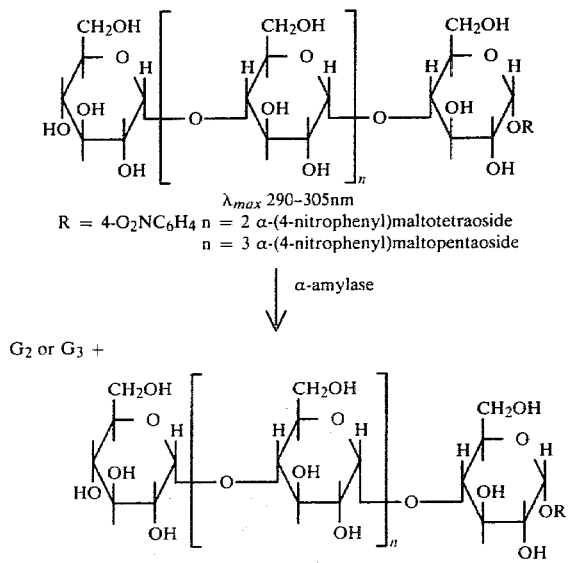

$\lambda_{max}$ 290–305nm
R = 4-O₂NC₆H₄ n = 2 α-(4-nitrophenyl)maltotetraoside
n = 3 α-(4-nitrophenyl)maltopentaoside

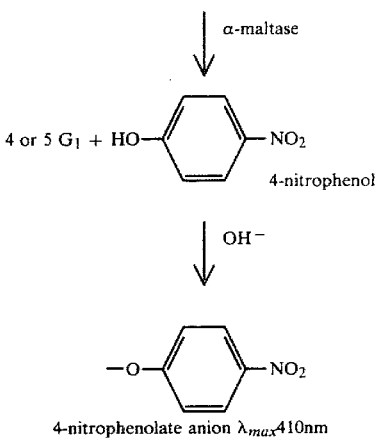

R = 4-O₂NC₆H₄ n = 0 α-(4-nitrophenyl)maltoside 4-nitrophenolate anion $\lambda_{max}$ 410nm The defined oligosaccharide substrate is added to a solution containing a measured amount of the sample to be tested; and the spectral absorbance of the solution is monitored, either as an end point determination or a rate determination using conventional techniques. Usually, as in all enzyme reactions, the reaction solution is maintained at a substantially constant pH and a substantially constant temperature. When these substances are used, it is desirable to perform the assay in a solution which has had its pH adjusted to the basic range in order to enhance the absorbance at 410 nm. For example, G₄pNp and G₅pNp ($\lambda_{max}$ 290–305 nm) and 4-nitrophenol ($\lambda_{max}$ 313 nm) have a low extinction coefficient at 410 nm compared to 4-nitrophenolate anion ($\lambda_{max}$ 410 nm).

To best accomplish this, a reagent test kit containing the defined substrate disclosed above and a maltase is used. One exemplary test kit is disclosed in U.S. Pat. No. 3,476,515. This test kit can be used in the analyzer described in U.S. Pat. No. 3,770,382.

EXAMPLE 1

A sample of α-(4-nitrophenyl) maltotetraoside (G₄pNp) prepared in accordance with Example 1H of U.S. Patent Application Ser. No. 704,975, filed on the same day as this application, was dissolved in 66.7 mM sodium phosphate buffer, pH 6.5, to provide various substrate concentrations ranging from 2 to 8 mg/3 ml. As described in U.S. Ser. No. 704,975, this substrate sample has been purified using a Sephadex ® LH-20 Chromatographic Column. α-Glucosidase of various concentrations ranging from 2.5 to 12.5 International Units per three milliliters of solution (IU/3 ml) was then added to the substrate solution and the volume of the solution was brought up to 3.0 ml. The solution was incubated at 37° C. for 1 to 10 minutes.

After the blank rate was measured at 410 nm, using a Gilford spectrophotometer, the reaction was initiated by adding 0.1 ml of an Elevated Enzyme Control Product sold by the E. I. du Pont de Nemours and Company (1150 Somogyi Units per deciliter (SU/dl) amylase) diluted 1:1 with Du Pont Enzyme Diluent. This level of amylase is approximately six times the upper normal serum level. The total reaction rate was then measured using the Gilford spectrophotometer, and by subtracting the blank rate from the total rate, the net reaction rate was obtained.

A two-variable statistical optimization for the substrate and the α-glucosidase was run. The results of this evaluation are given in Table I in arbitrary Absorbance units (A) per minute.

TABLE I

|  |  | 2.0 | 5.0 | 8.0 |
|---|---|---|---|---|
|  |  | .005[1] | .012 | .018 |
|  | 2.5 | .091[2] | .113 | .110 |
|  |  | .086[3] | .101 | .092 |
|  |  | .004 | .008 | .011 |
| α-gluco- | 5 | .090 | .110 | .109 |
| sidase (IU/3ml.) |  | .086 | .102 | .098 |
|  |  | .001 | .008 | .002 |
|  | 5 | .079 | .091 | .080 |
|  |  | .078 | .083 | .078 |

G4pNp mg/3 ml

[1] Blank rate (A/min)
[2] Total rate (A/min)
[3] Net rate (A/min)

From this evaluation, it can be seen that the blank rate increases as the concentrations of both the G4pNp and the α-glucosidase increase, that the optimum concentration of G4pNp is approximately 4.0 mg/3 ml, and that the optimum concentration of α-glucosidase is approximately 7.5 IU/3 ml.

Using these optimum values of G4pNp and α-glucosidase in a reaction solution of 3 ml, the reaction rates for various amylase sample concentrations were measured and a standard curve was generated. From this curve, the sensitivity in mA/min/SU/dl was measured. The standard curve for this sample is given in FIG. 1; the blank rate and sensitivity are given for this and other examples in Table II.

TABLE II

| Example | Blank Rate (mA/min) | Sensitivity (mA/min/SU/dl) |
|---|---|---|
| 1 | 5.0 | 0.115 |
| 2 | not measured | 0.231 |
| 3 | 10.3–13.3 | 0.110 |
| 4 | 3.0 | 0.116 |

EXAMPLE 2

A small amount of the substrate sample used in Example 1 was further purified by High Performance Liquid Chromatography (HPLC) which is a standard purification technique, well known to those skilled in the art. Using the optimum values for G4pNp and α-glucosidase obtained in Example 1, and the amylase sample of Example 1, a standard curve was generated using this purified substrate. The sensitivity was also obtained, as described in Example 1. The standard curve is given in FIG. 1, the sensitivity is given in Table II. As can be seen from Table II, the sensitivity of the assay was increased markedly by the purification, indicating that the substrate sample of Example 1 contained some inhibitor.

EXAMPLE 3

The α-(4-nitrophenyl) maltotetraoside (G4pNp) sample used in this Example was obtained by deacetylation of the HPLC purified acetate of Example 1D of U.S. Patent Application Ser. No. 704,975. In particular, to a sample of this acetate, a solution of sodium methoxide and methanol was added and the solution was stirred at room temperature in a closed vessel for 18 hours. The methanol was then removed under reduced pressure.

The G4pNp so formed was dissolved in 66.7 mM sodium phosphate buffer, pH 6.5, to provide a substrate concentration of 4 mg/3 ml. Then 7.5 IU/3 ml of α-glucosidase was added to the substrate solution and the volume of the solution was brought up to 3.0 ml. The solution was incubated at 37° C. for one to ten minutes.

After the blank rate was measured, as described in Example 1 above, the reaction was incubated by adding 0.1 ml of Du Pont Elevated Enzyme Control Product, diluted 1:1 with Du Pont Enzyme Diluent. The reaction rates for various amylase sample concentrations were measured as discussed in Example 1 above, and a standard curve was generated. From this curve, the sensitivity in mA/min/SU/dl was measured. The standard curve for this substrate is given in FIG. 1; the blank rate and sensitivity are given in Table II.

This is a crude sample; one that has not been purified by chromatographic separation techniques. As a result, the blank rate is very high, ranging from 10.3 to 13.3 mA/min, but the sensitivity is equivalent to that of the substrate reported in Example 1 where initial purification was accomplished using a Sephadex ® LH-20 column.

Another series of reactions were run using the conditions described above, except that five minutes after it was initiated, the reaction was quenched by adding a 1.5 ml aliquot of the sample solution into either 1.5 ml of 0.2 M $Na_2CO_3$ or 5 ml of 0.002 N NaOH. At pH 6.5, the extinction coefficient of the 4-nitrophenol is relatively low because the 4-nitrophenol is not all ionized. The increase in pH caused by the quenching is sufficient to completely ionize the 4-nitrophenol to 4-nitrophenylate anion, thereby increasing the extinction coefficient. This gives rise to an "end point" determination for which the standard curves were non-linear, probably because the system was optimized for a rate and not an end-point approach. However, a five to ten fold increase in sensitivity was observed.

EXAMPLE 4

A sample of α-(4-nitrophenyl) maltotetraoside, prepared in accordance with Example 1G of U.S. Patent Application Ser. No. 704,975, was dissolved in 66.7 mM sodium phosphate buffer, pH 6.5, to provide a substrate concentration of 4 mg/3 ml. Then 7.5 IU/3 ml of α-glucosidase was added to the substrate solution and the volume of the solution was brought up to 3.0 ml. The solution was incubated at 37° C. for one to ten minutes.

After the blank rate was measured in a Gilford spectrophotometer at 410 nm, the reaction was initiated by adding 0.1 ml of the Du Pont Elevated Enzyme Control Product, diluted 1:1 with Du Pont Enzyme Diluent. The reaction rates for the various amylase sample concentrations were measured, using the Gilford spectrophotometer, and a standard curve was generated. From this curve, the sensitivity in mA/min/SU/dl was measured. The standard curve for this sample is given in FIG. 1; the blank rate and sensitivity are given in Table II.

This again is a substrate that was purified by using a Sephadex ® LH-20 column. The sensitivity of the assay using the substrate of this Example is equivalent to that of the assay reported in Examples 1 and 3. The blank rate, however, is somewhat lower than that of Example 1 and considerably lower than that of Example 3.

EXAMPLE 5

A sample of α-(4-nitrophenyl) maltopentaoside ($G_5pNp$), prepared in accordance with Example 2E of U.S. Patent Application Ser. No. 704,975, was dissolved in 66.7 mM sodium phosphate buffer, pH 6.5, to provide various substrate concentrations ranging from 4.0 to 12.0 mg/3 ml. α-Glucosidase of various activity ranging from 15 to 45 IU/3 ml was then added to the substrate solution and the volume of the solution was brought up to 3.0 ml. The solution was incubated at 37° C. for one to ten minutes.

Initial tests were conducted using 4.0 mg/3 ml $G_5pNp$ and three α-glucosidase concentrations, 7.0, 14.0, and 28.0 IU/3 ml. For each of these three concentrations, as set forth in Example 1, the standard curves were produced using the amylase sample identified in Example 1. In each case, the blank rate was 3.0 mA/min. The standard curve for the three α-glucosidase concentrations are given in FIG. 2. All curves were non-linear which made a determination of the sensitivity difficult. Sensitivity, however, is estimated to be greater than 0.160 mA/min/IU/dl. Linearity increased as α-glucosidase concentration increased indicating that the α-glucosidase concentration was suboptimal.

A two-variable optimization was performed as described in Example 1. The results of this optimization are given in Table III.

TABLE III

| | | .003[1] | .004 | .005 |
|---|---|---|---|---|
| | 45 | .128[2] | .139 | .145 |
| | | .125[3] | .135 | .140 |
| | | .003 | .004 | .012 |
| α-gluco-sidase (IU/3ml.) | 30 | .122 | .135 | .133 |
| | | .119 | .131 | .121 |
| | | .003 | .005 | .007 |
| | 15 | .110 | .119 | .114 |
| | | .107 | .114 | .107 |
| | | 4.0 | 8.0 | 12.0 |
| | | $G_5pNp$ mg/3 ml | | |

[1,2,3] see Table I

From this evaluation, it can be seen that there is little increase in the blank rate as $G_5pNp$ or α-glucosidase concentrations are increased. This is consistent with the situation with $G_5$ as explained above. This analysis also indicates that the optimum value for either $G_5pNp$ or α-glucosidase has not been reached at 12.0 mg/3 ml or 45 IU/3 ml, respectively.

In the sense that $G_5pNp$ has a lower or at least a stable blank rate as a function of substrate and α-glucosidase concentrations, it is a preferred substrate. However, the large concentrations of $G_5pNp$ and α-glucosidase required for the assay decreases its preferred status.

The disclosure above is intended to instruct those skilled in the art, and is not intended to limit the scope of the invention. Many modifications well within the skill of the art are intended to be included with the scope of the invention as set forth in the appended claims.

What is claimed is:

1. A method for the rapid determination of the amylase content of a sample comprising the amylase content of a sample comprising the steps of:
   (a) adding to a solution containing a measured amount of the sample a defined polysaccharide substrate having the following formula:

$$\begin{array}{c}\text{CH}_2\text{OH} \\ \text{HO} \end{array} \begin{bmatrix} \text{CH}_2\text{OH} \\ \end{bmatrix}_n \begin{array}{c} \text{CH}_2\text{OH} \\ \text{OR} \end{array}$$

where n is 2, 3, or 4, and R is a substituted aromatic radical which, as a detached aglycone, exhibits a different spectral absorbance than the substrate;
   (b) adding a maltase to the solution; and
   (c) monitoring the spectral absorbance of the solution.

2. The method of claim 1 wherein R is a substituted aromatic radical selected from the group consisting of

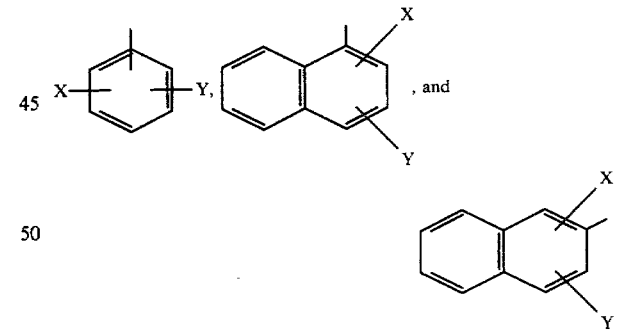

, and in which X and Y are individually selected from the group consisting of H, $NO_2$, halogens, alkyls of from 1 to 4 carbon atoms, OR' or $CO_2R'$, where R' is an alkyl of from 1 to 6 carbon atoms, and at least one of X and Y is $NO_2$.

3. The method of claim 2 wherein R is

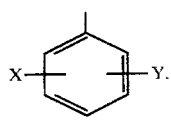

4. The method of claim 1 wherein the maltase is α-glucosidase.

5. The method of claim 1 wherein R is 4-nitrophenyl.

6. The method of claim 5 wherein the solution is maintained at a substantially constant pH in the basic range and a substantially constant temperature and wherein the spectral absorbance is within one hour of adding the sample to the substrate.

7. The method of claim 2 wherein the solution is maintained at a substantially constant pH in the basic range and at a substantially constant temperature.

8. In a method for rapidly determining the amylase content of a sample comprising the steps of adding a maltase and a substrate to a solution containing a measured amount of the sample and monitoring the change in spectral absorbance of the solution, the improvement wherein the substrate is α-(4-nitrophenyl) glucoside of maltotetraose, maltopentaose or maltohexaose.

9. A reagent test kit for rapidly determining the amylase content of a sample comprising:

(a) a defined polysaccharide substrate having the following formula:

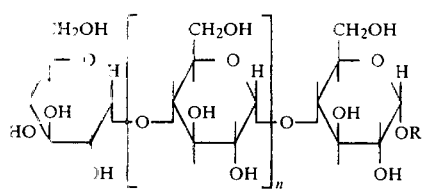

wherein n is 2, 3 or 4, and R is a substituted aromatic radical which, when detached from the polysaccharide in the form of a phenolate anion, exhibits a different spectral absorbance than the substrate; and (b) maltase.

10. The test kit of claim 9 wherein R is a substituted aromatic radical selected from the group consisting of

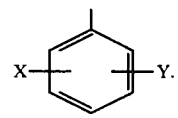

in which X and Y are individually selected from the group consisting of H, NO$_2$, halogens, alkyls of from 1 to 4 carbon atoms, OR' or CO$_2$R', where R' is an alkyl of from 1 to 6 carbon atoms, and at least one of X and Y is NO$_2$.

11. The test kit of claim 10 wherein the maltase is α-glucosidase.

12. The test kit of claim 10 wherein R is

13. The test kit of claim 10 wherein R is 4-nitrophenyl.

14. In a test kit for rapidly determining the amylase content of a sample comprising a maltase and a substrate, the improvement wherein the substrate is α-(4-nitrophenyl) glycoside of maltotetraose, maltopentaose, or maltohexaose.

15. A process for determining the α-amylase content of a sample comprising the steps of adding an oligosaccharide substrate, having 4–6 glucose units and a terminal 4-nitrophenyl group to a solution containing a measured amount of said sample and α-glucosidase and determining amylase activity by the release of p-nitrophenol.

* * * * *